United States Patent [19]

Commercon et al.

[11] Patent Number: 5,637,723
[45] Date of Patent: Jun. 10, 1997

[54] PROCESS FOR PREPARING TAXANE DERIVATIVES

[75] Inventors: Alain Commercon, Vitry-Sur-Seine; Eric Didier, Paris; Elie Fouque, Saint Maur Des Fosses, all of France

[73] Assignee: Rhone-Poulenc Rorer S.A., Antony, France

[21] Appl. No.: 406,985

[22] PCT Filed: Oct. 4, 1993

[86] PCT No.: PCT/FR93/00968

§ 371 Date: Apr. 4, 1995

§ 102(e) Date: Apr. 4, 1995

[87] PCT Pub. No.: WO94/07878

PCT Pub. Date: Apr. 14, 1994

[30] Foreign Application Priority Data

Oct. 5, 1992 [FR] France ............... 92/11742

[51] Int. Cl.$^6$ ............... C07D 413/02; C07D 263/04
[52] U.S. Cl. ............... 548/215; 549/510
[58] Field of Search ............... 549/510; 548/215

[56] References Cited

U.S. PATENT DOCUMENTS 5,440,056  8/1995  Klein et al. ............... 549/510
5,476,954  12/1995  Bourzat et al. ............... 549/510

FOREIGN PATENT DOCUMENTS

WO92/09589  6/1992  WIPO .
WO93/16060  8/1993  WIPO .

*Primary Examiner*—C. Warren Ivy
*Assistant Examiner*—Lyman H. Smith
*Attorney, Agent, or Firm*—Finnegan, Henderson, Farabow, Garrett & Dunner, L.L.P.

[57] ABSTRACT

Method of preparing taxane derivatives of general formula (I) by esterification of protected baccatine III or 10-deacetylbaccatine III by means of an acid of general formula (VII), deprotection of the side chain and elimination of the hydroxy function protection groupings. In general formulae (I) and (VII): Ar stands for aryl, R is hydrogen or acetyl, $R_1$ is benzoyl or $R_2$—O—CO— in which $R_2$ is alkyl, alkenyl, alkynyl, cycloalkyl, cycloalkenyl, bicycloalkyl, phenyl or heterocyclyl, and $R_3$ is hydrogen, alkoxy, optionally substituted aryl.

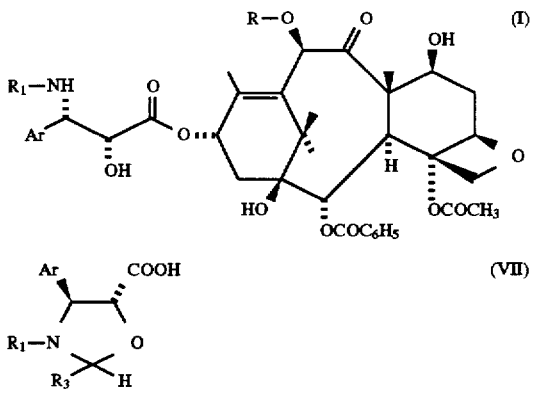

36 Claims, No Drawings

PROCESS FOR PREPARING TAXANE DERIVATIVES

DESCRIPTION OF THE INVENTION

This application is a 35 U.S.C. 371 National Stage filing of PCT/FR93/00968 published as WO 94/07878 on Apr. 14, 1994.

The present invention relates to a new process for preparing taxane derivatives of general formula:

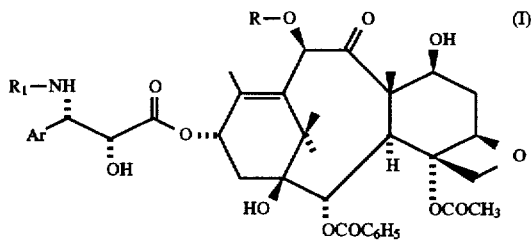

which possess noteworthy antileukaemic and antitumor properties.

In the general formula (I): R represents a hydrogen atom or an acetyl radical, $R_1$ represents a benzoyl radical or a radical $R_2$—O—CO— in which $R_2$ represents an alkyl, alkenyl, alkynyl, cycloalkyl, cycloalkenyl, bicycloalkyl, phenyl or nitrogenous heterocyclic radical, and Ar represents an aryl radical.

More especially, R represents a hydrogen atom or an acetyl radical and $R_1$ represents a benzoyl radical or a radical $R_2$—O—CO— in which $R_2$ represents:

an unbranched or branched alkyl radical containing 1 to 8 carbon atoms, an alkenyl radical containing 2 to 8 carbon atoms, an alkynyl radical containing 3 to 8 carbon atoms, a cycloalkyl radical containing 3 to 6 carbon atoms, a cycloalkenyl radical containing 4 to 6 carbon atoms or a bicycloalkyl radical containing 7 to 10 carbon atoms, these radicals being optionally substituted with one or more substituents chosen from halogen atoms and hydroxyl radicals, alkyloxy radicals containing 1 to 4 carbon atoms, dialkylamino radicals in which each alkyl portion contains 1 to 4 carbon atoms, piperidino or morpholino radicals, 1-piperazinyl radicals (optionally substituted at position 4 with an alkyl radical containing 1 to 4 carbon atoms or with a phenylalkyl radical in which the alkyl portion contains i to 4 carbon atoms), cycloalkyl radicals containing 3 to 6 carbon atoms, cycloalkenyl radicals containing 4 to 6 carbon atoms, phenyl, cyano or carboxyl radicals or alkyloxycarbonyl radicals in which the alkyl portion contains 1 to 4 carbon atoms, or a phenyl radical optionally substituted with one or more atoms or radicals chosen from alkyl radicals containing 1 to 4 carbon atoms or alkyloxy radicals containing 1 to 4 carbon atoms, or a saturated or unsaturated 5- or 6-membered nitrogenous heterocyclic radical optionally substituted with one or more alkyl radicals containing 1 to 4 carbon atoms, on the understanding that the cycloalkyl, cycloalkenyl or bicycloalkyl radicals can be optionally substituted with one or more alkyl radicals containing 1 to 4 carbon atoms, and Ar represents a phenyl or α- or β-naphthyl radical optionally substituted with one or more atoms or radicals chosen from halogen (fluorine, chlorine, bromine, iodine) atoms and alkyl, alkenyl, alkynyl, aryl, arylalkyl, alkoxy, alkylthio, aryloxy, arylthio, hydroxyl, hydroxyalkyl, mercapto, formyl, acyl, acylamino, aroylamino, alkoxycarbonylamino, amino, alkylamino, dialkylamino, carboxyl, alkoxycarbonyl, carbamoyl, dialkylcarbamoyl, cyano and trifluoromethyl radicals, on the understanding that the alkyl radicals and alkyl portions of the other radicals contain 1 to 4 carbon atoms, and that the alkenyl and alkynyl radicals contain 3 to 8 carbon atoms and the aryl radicals are phenyl or α- or β-naphthyl radicals.

Of very special importance are the products of general formula (I) in which R represents a hydrogen atom or an acetyl radical, $R_1$ represents a benzoyl or t-butoxycarbonylamino radical and Ar represents a phenyl radical.

The products of general formula (I) in which $R_1$ represents a benzoyl radical correspond to taxol and to 10-deacetyltaxol, and the products of general formula (I) in which $R_1$ represents a t-butoxycarbonyl radical correspond to those which form the subject of European Patent 0,253,738.

According to the process which is described in International Application PCT WO 92/09,589, the derivatives of general formula (I) may be obtained by:

condensation of an oxazolidine derivative of general formula:

in which Ar is defined as above, Boc represents a t-butoxycarbonyl radical and $R'_2$ and $R'_3$, which may be identical or different, represent an alkyl radical containing 1 to 4 carbon atoms optionally substituted with one or more aryl radicals, or an aryl radical, or alternatively $R'_2$ and $R'_3$, together with the carbon atom to which they are linked, form a 4- to 7-membered ring, with protected 10-deacetylbaccatin III or baccatin III of general formula:

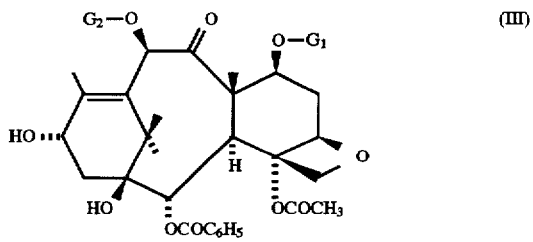

in which $G_1$ represents a group protecting the hydroxyl function and $G_2$ represents an acetyl radical or a group protecting the hydroxyl function, to obtain a product of general formula:

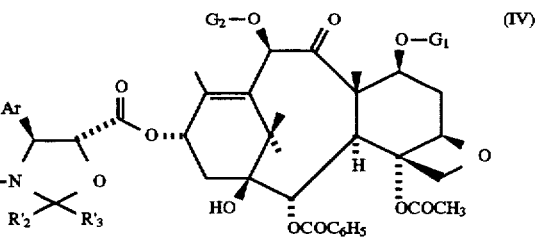

in which Ar, $R'_2$, $R'_3$, $G_1$, $G_2$ and Boc are defined as above, treatment of the product of general formula (IV) in an acid medium under conditions which have no effect on $G_1$ and $G_2$, to obtain the product of general formula:

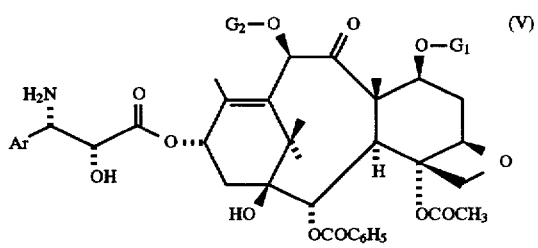

in which Ar, $G_1$ and $G_2$ are defined as above, treatment of the product of general formula (V) with a suitable reagent for introducing a benzoyl radical or radical $R_2$—O—CO—, to obtain a product of general formula:

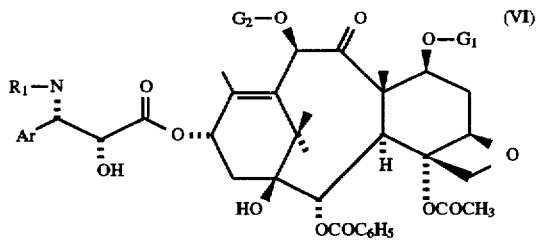

in which Ar, $R_1$, $G_1$ and $G_2$ are defined as above, and replacement of the protective groups $G_1$ and $G_2$ of the product of general formula (VI) by hydrogen atoms to obtain the product of general formula (I).

It has now been found, and this forms the subject of the present invention, that the products of general formula (I) may be obtained by:

condensation of an acid of general formula:

in which Ar and $R_1$ are defined as above and $R_3$ represents a hydrogen atom or an alkoxy radical containing 1 to 4 carbon atoms or an optionally substituted aryl radical, or of a derivative of this acid, with baccatin III or 10-deacetylbaccatin III of general formula (III) in which $G_1$ represents a group protecting the hydroxyl function and $G_2$ represents an acetyl radical or a group protecting the hydroxyl function, to obtain a product of general formula:

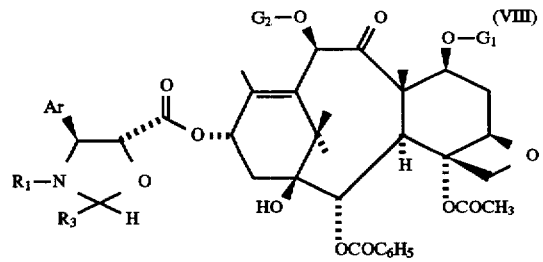

in which Ar, $R_1$, $R_3$, $G_1$ and $G_2$ are defined as above, deprotection of the side chain and, where appropriate, of the hydroxyl functions protected by $G_1$ and $G_2$ to obtain a product of general formula:

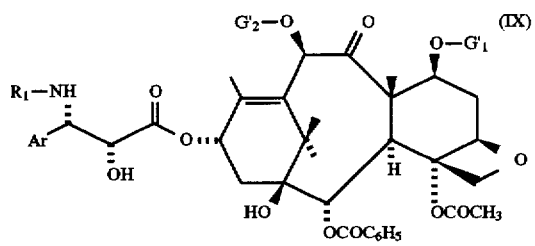

in which Ar and $R_1$ are defined as above. $G'_1$ represents a hydrogen atom or a group protecting the hydroxyl function and $G'_2$ represents a hydrogen atom or an acetyl radical or a group protecting the hydroxyl function, and then where appropriate, replacement of the protective groups $G'_1$ and, where appropriate, $G'_2$ of the product of general formula (IX) by hydrogen atoms to obtain a product of general formula (I).

According to the invention, the esterification of the product of general formula (III) is performed by means of an acid of general formula (VII), optionally in the form of an anhydride or in the form of a halide or mixed anhydride.

It is preferable to use an acid of general formula (VII), or its activated derivatives, in which $R_3$ represents a hydrogen atom or an alkoxy radical containing 1 to 4 carbon atoms or a phenyl radical optionally substituted with one or more electron-donating radicals chosen more especially from the group comprising alkoxy radicals containing 1 to 4 carbon atoms.

The esterification by means of an acid of general formula (VII) may be performed in the presence of a condensing agent, for instance a carbodiimide such as dicyclohexylcarbodiimide or a reactive carbonate such as di-2-pyridyl carbonate, and an activating agent, for instance an aminopyridine such as 4-(dimethylamino)-pyridine or 4-pyrrolidinopyridine, working in an organic solvent chosen from ethers such as tetrahydrofuran, diisopropyl ether, methyl t-butyl ether or dioxane, ketones such as methyl isobutyl ketone, esters such as ethyl acetate, isopropyl acetate or n-butyl acetate, nitriles such acetonitrile, aliphatic hydrocarbons such as pentans, hexane or heptane, halogenated aliphatic hydrocarbons such as dichloromethane or 1,2-dichloroethane or aromatic hydrocarbons such as benzene, toluene, xylenes, ethylbenzene, isopropylbenzene or chlorobenzene, at a temperature of between −10° and 90° C. It is especially advantageous to perform the esterification working in an aromatic solvent at a temperature in the region of 20° C.

The esterification may also be carried out using the acid of general formula (VII) in the form of an anhydride of formula:

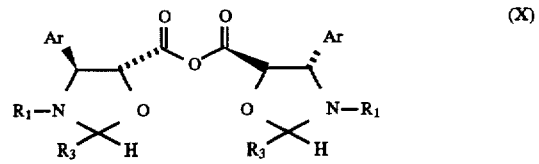

in which Ar, $R_1$ and $R_3$ are defined as above, in the presence of an activating agent, for instance an aminopyridine such as 4-(dimethylamino)pyridine, working in an organic solvent chosen from ethers such as tetrahydrofuran, diisopropyl ether, methyl t-butyl ether or dioxane, ketones such as methyl isobutyl ketone, esters such as ethyl acetate, isopropyl acetate or n-butyl acetate, nitriles such as acetonitrile, aliphatic hydrocarbons such as pentane, hexane or heptane, halogenated aliphatic hydrocarbons such as dichloromethane or 1,2-dichloroethane or aromatic hydrocarbons such as benzene, toluene, xylenes, ethylbenzene, isopropylbenzene or chlorobenzene, at a temperature of between 0° and 90° C.

The esterification may also be carried out using the acid of general formula (VII) in the form of a halide or in the form of a mixed anhydride of general formula:

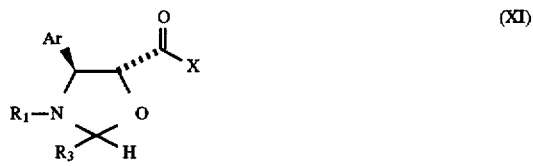
(XI)

in which Ar, $R_1$ and $R_3$ are defined as above and X represents a halogen atom or an acyloxy or aroyloxy radical, optionally prepared in situ, in the presence of a base which is preferably a nitrogenous organic base, for instance a tertiary aliphatic amine such as triethylamine, pyridine, an aminopyridine such as 4-(dimethylamino)pyridine or 4-pyrrolidinopyridine, working in an inert organic solvent chosen from ethers such as tetrahydrofuran, diisopropyl ether, methyl t-butyl ether or dioxane, esters such as ethyl acetate, isopropyl acetate or n-butyl acetate, nitriles such as acetonitrile, aliphatic hydrocarbons such as pentane, hexane or heptane, halogenated aliphatic hydrocarbons such as dichloromethane or 1,2-dichloroethane and aromatic hydrocarbons such as benzene, toluene, xylenes, ethylbenzene, isopropylbenzene or chlorobenzene, at a temperature of between 10° and 80° C., and preferably in the region of 20° C.

It is preferable to use an activated derivative of general formula (XI) in which X represents a halogen atom or an acyloxy radical containing 1 to 5 carbon atoms or an aroyloxy radical in which the aryl portion is a phenyl radical optionally substituted with 1 to 5 identical or different atoms or radicals chosen from halogen (chlorine, bromine) atoms and nitro, methyl or methoxy radicals.

The deprotection of the side chain may be performed in the presence of an inorganic acid (hydrochloric acid, sulphuric acid) or organic acid (acetic acid, methanesulphonic acid, trifluoromethane-sulphonic or p-toluenesulphonic acid) used alone or mixed, working in an organic solvent chosen from alcohols (methanol, ethanol, propanol, isopropanol), ethers (tetrahydrofuran, diisopropyl ether, methyl t-butyl ether), esters (ethyl acetate, isopropyl acetate, n-butyl acetate), aliphatic hydrocarbons (pentane, hexane, heptane), halogenated aliphatic hydrocarbons (dichloromethane, 1,2-dichloroethane), aromatic hydrocarbons (benzene, toluene, xylenes) and nitriles (acetonitrile), at a temperature of between −10° and 60° C., and preferably between 15° and 30° C. The inorganic or organic acid may be used in a catalytic or stoichiometric amount or in excess.

The deprotection may also be carried out under oxidizing conditions using, for example, ammonium cerium IV nitrate in an acetonitrile/water mixture or 2,3-dichloro-5,6-dicyano-1,4-benzoquinone in water.

The deprotection may also be carried out under reducing conditions, for example by hydrogenolysis in the presence of a catalyst.

The protective groups $G_1$ and $G_2$ are preferably 2,2,2-trichloroethoxycarbonyl or 2-(2-trichloromethylpropoxy)carbonyl radicals or trialkylsilyl, dialkylarylsilyl, alkyldiarylsilyl or triarylsilyl radicals in which the alkyl portions contain 1 to 4 carbon atoms and the aryl portions are preferably phenyl radicals.

Replacement of the protective groups $G_1$ and, where appropriate, $G_2$ representing a silyl radical by hydrogen atoms may be performed simultaneously with deprotection of the side chain.

Replacement of the protective groups $G_1$ and, where appropriate, $G_2$ representing a 2,2,2-trichloroethoxycarbonyl or 2-(2-trichloromethylpropoxy)carbonyl radical is performed with zinc, optionally in combination with copper, in the presence of acetic acid at a temperature of between 20° and 60° C., or by means of an inorganic or organic acid such as hydrochloric acid or acetic acid dissolved in an aliphatic alcohol containing 1 to 3 carbon atoms or in an aliphatic ester such as ethyl acetate, isopropyl acetate or n-butyl acetate, in the presence of zinc optionally in combination with copper.

This replacement may also be performed by electrolytic reduction.

The acid of general formula (VII) may be obtained by saponification in a basic medium of an ester of general formula:

(XII)

in which Ar, $R_1$ and $R_3$ are defined as above and $R_4$ represents an alkyl radical containing 1 to 4 carbon atoms optionally substituted with a phenyl radical.

In general, the saponification is performed by means of an inorganic base such as an alkali metal hydroxide (lithium, potassium, sodium hydroxide) or an alkali metal carbonate or bicarbonate (sodium bicarbonate, potassium carbonate or bicarbonate), in an aqueous-alcoholic medium such as a methanol/water mixture at a temperature of between 10° and 40° C., and preferably in the region of 20° C.

The ester of general formula (XII) may be obtained by the action of an aldehyde of general formula:

(XIII)

in which $R_3$ is defined as above, optionally in the form of a dialkyl acetal or an enol alkyl ether or an orthoformate of general formula:

(XIV)

in which $R_3$ is defined as above, on a phenylisoserine derivative of general formula:

(XV)

in which Ar, $R_1$ and $R_4$ are defined as above, preferably in the 2R,3S form, working in an inert organic solvent in the presence of a strong inorganic acid such as sulphuric acid or strong organic acid such as p-toluenesulphonic acid, optionally in the form of a pyridinium salt, at a temperature between 0° C. and the boiling point of the reaction mixture. Solvents which are especially suitable are aromatic hydrocarbons.

The phenylisoserine derivative of general formula (XV) may be obtained by acylation of a phenylisoserine derivative of general formula:

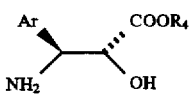

in which Ar and $R_4$ are defined as above.

The acylation is performed by the action of benzoyl chloride or a reactive derivative of general formula:

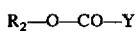

in which $R_2$ is as defined above and Y represents a halogen (fluorine, chlorine) atom or a residue —O—$R_2$ or —O—CO—O—$R_2$ working in an organic solvent, for instance an aliphatic ester such as ethyl acetate or a halogenated aliphatic hydrocarbon such as dichloromethane, in the presence of an inorganic or organic base such as sodium bicarbonate. In general, the reaction is performed at a temperature of between 0° and 50° C., and preferably in the region of 20° C.

The product of general formula (XVI) may be prepared under the conditions described in International Application PCT WO 92/09,589.

The anhydride of general formula (X) may be obtained by reacting a dehydrating agent such as dicyclohexylcarbodiimide with the acid of general formula (VII), working in an organic solvent chosen from ethers such as tetrahydrofuran, diisopropyl ether, methyl t-butyl ether or dioxane, ketones such as methyl isobutyl ketone, esters such as ethyl acetate, isopropyl acetate or n-butyl acetate, nitriles such as acetonitrile, aliphatic hydrocarbons such as pentans, hexane or heptane, halogenated aliphatic hydrocarbons such as dichloromethane or 1,2-dichloroethane or aromatic hydrocarbons such as benzene, toluene, xylenes, ethylbenzene, isopropylbenzene or chlorobenzene, at a temperature of between 0° and 30° C.

The activated acid of general formula (XI) may be obtained by the action of a sulphuryl halide, preferably the chloride, or a product of general formula:

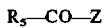

in which $R_5$ represents an alkyl radical containing 1 to 4 carbon atoms or a phenyl radical optionally substituted with 1 to 5 identical or different atoms or radicals chosen from halogen atoms and nitro, methyl and methoxy radicals and Z represents a halogen atom, preferably a chlorine atom, on an acid of general formula (VII), working in a suitable organic solvent such as tetrahydrofuran in the presence of an organic base, for instance a tertiary amine such as triethylamine, at a temperature of between 0° and 30° C.

The process according to the present invention is especially useful for preparing the products of general formula (I) in which R represents a hydrogen atom or an acetyl radical, $R_1$ represents a benzoyl or t-butoxycarbonyl radical and Ar represents an optionally substituted phenyl radical.

EXAMPLES

The examples which follow illustrate the present invention.

EXAMPLE 1

A solution of 10.0 g of methyl (2R, 3S)-3-t-butoxycarbonylamino-2-hydroxy-3-phenylpropionate and 0.25 g of pyridinium p-toluenesulphonate in 200 cm³ of toluene is dehydrated by distilling off 20 cm³ of solvent. 6.34 cm³ of p-methoxybenzaldehyde dimethyl acetal are added in the course of 5 minutes to the reaction mixture heated to boiling. During the addition, 50 cm³ of solvent are distilled off, and then a further 100 cm³ of solvent are distilled off. After cooling to a temperature in the region of 20° C., 80 cm³ of cyclohexane are added in the course of 10 minutes. The mixture is cooled to 0°–5° C. The slurry obtained is filtered on sintered glass and the filter cake is washed with 40 cm³ of cyclohexane and then dried under reduced pressure at a temperature in the region of 20° C. 10.39 g of (2R,4S,5R)-3-t-butoxycarbonyl-2-(4-methoxyphenyl)-4-phenyl-5-methoxycarbonyl-1,3-oxazolidine, the characteristics of which are as follows, are thereby obtained in a 74% yield:

infrared spectrum (in disk with KBr): characteristic absorption bands at 3100–3000, 2980, 2960, 2930, 2910, 2840, 1740, 1700, 1614, 1514, 1460, 1435, 1390, 1370, 1245, 1175, 1165, 816, 760 and 700 cm⁻¹ proton nuclear magnetic resonance spectrum (400 MHz; CDCl₃; temperature: 323° K.; chemical shifts δ in ppm; coupling constants J in Hz): 1.11 (s, 9H); 3.60 (s, 3H); 3.82 (s, 3H); 4.58 (d, J=5, 1H); 5.42 (broad d, J=5, 1H); 6.38 (s large, 1H); 6.92 (d, J=7.5, 2H); 7.30 to 7.45 (mt, 7H).

14 cm³ of an aqueous solution containing 0.31 g of lithium hydroxide monohydrate are added to a solution of 3.0 g of the product obtained above in 27 cm³ of methanol. The mixture is stirred for 2 hours at a temperature in the region of 20° C. The methanol is removed by distillation under reduced pressure and 40 cm³ of dichloromethane are then added. With vigorous stirring, the reaction mixture is acidified by adding 1N hydrochloric acid until the pH equals 1. After settling has taken place, the aqueous phase is separated and extracted twice with 40 cm³ of dichloromethane. The combined organic phases are dried over sodium sulphate. After filtration and evaporation of the solvent, 2.88 g of (2R,4S,5R)-3-t-butoxycarbonyl-2-(4-methoxyphenyl)-4-phenyl-1,3-oxazolidine-5-carboxylic acid, the characteristics of which are as follows, are obtained in a 94.5% yield:

infrared spectrum (in disk with KBr): characteristic absorption bands at 3325–2675, 2980, 2955, 2935, 2845, 1755, 1700, 1615, 1590, 1515, 1460, 1250, 1175, 1030, 835, 765 and 705 cm⁻¹ proton nuclear magnetic resonance spectrum (250 MHz; CDCl₃; chemical shifts a in ppm; coupling constants J in Hz): 1.08 (s, 9H); 3.82 (s, 3H); 4.61 (d, J=5, 1H); 5.42 (broad d, J=5, 1H); 6.38 (broad s, 1H); 6.92 (d, J=7.5 2H); 7.30 to 7.45 (mt, 7H).

EXAMPLE 2

0.52 g of dicyclohexylcarbodiimide is added at 0° C. to a stirred solution of 1.0 g of (2R,4S,5R)-3-t-butoxycarbonyl-2-(4-methoxyphenyl)-4-phenyl-1,3-oxazolidine-5-carboxylic acid, 1.34 g of 4,acetoxy-2α-benoyloxy-5β,20-epoxy-1,13α-dihydroxy-9-oxo-7β,10β-bis(2,2,2-trichloroethoxy)carbonyloxy-11-taxene and 0.061 g of 4-(dimethylamino)pyridine in 7.6 cm³ of anhydrous toluene. The mixture is stirred for 2 hours at a temperature of 20° C. The dicyclohexylurea is separated by filtration and washed with toluene. The combined organic phases are washed with 0.1N hydrochloric acid solution and saturated sodium hydrogen carbonate solution and dried over sodium sulphate. After filtration and concentration to dryness under reduced pressure, 2.09 g of crude 4-acetoxy-2α-benzoyloxy-5β,20-epoxy-1-hydroxy-9-oxo-7β,10β-bis(2,2,2-trichloroethoxy)carbonyloxy-11-taxen-13α-yl (2R,4S,5R)-3-t-butoxycarbonyl-2-(4-methoxyphenyl)-4-phenyl-1,3-oxazolidine-5-carboxylate are obtained, the characteristics of which are as follows:

infrared spectrum (CHCl$_3$): characteristic absorption bands at 3575, 1765, 1740, 1725, 1710, 1615, 1515, 1455, 1250, 1175, 980, 710 and 700 cm$^{-1}$ proton nuclear magnetic resonance spectrum (400 MHz; CDCl$_3$; temperature: 323° K.; chemical shifts δ in ppm; coupling constants J in Hz): 1.09 (s, 9H); 1.18 (s, 3H); 1.27 (s, 3H); 1.67 (s, 3H); 1.72 (s, 1H); 1.82 (s, 3H); 1.90 (s, 3H); 2.02 (m, 1H); 2.13 (dd, J=15 and 9, 1H); 2.25 (dd, J=15 and 9, 1H); 2.60 (mt, 1H); 3.83 (d, J=7, 1H); 3.83 (s, 3H); 4.12 (d, J=8, 1H); 4.26 (d, J=8, 1H); 4.60 (d, J=5, 1H); 4.61 (d, J=12, 1 H); 4.78 (limiting ab, J=11, 2H); 4.90 (broad d, J=10, 1H); 4.90 (d, J=12, 1H); 5.45 (broad d, J=5, 1H); 5.50 (dd, J=11 and 7, 1H); 5.66 (d, J=7, 1H); 6.12 (t, J=9, 1H); 6.18 (s, 1H); 6.39 (broad s); 6.94 (d, J=7.5, 2H); 7.42 (d, J=7.5, 2H); 7.35 to 7.50 (mt, 5H); 7.49 (t, J=5, 2H); 7.63 (t, J=7.5, 1H); 8.03 (d, J=7.5, 2H).

9 μl of 37% (w/w) aqueous hydrochloric acid solution are added to a solution of 0.161 g of the product obtained above in 2.1 cm$^3$ of ethyl acetate. The mixture is stirred for 3 hours at a temperature in the region of 20° C. Assay by high performance liquid chromatography shows that the yield of 4-acetoxy-2α-benzoyloxy-5β,20-epoxy-1-hydroxy-9-oxo-7β,10β-bis(2,2,2-trichloroethoxy)carbonyloxy-11-taxen-13α-yl (2R,3S)-3-t-butoxycarbonylamino-3-phenyl-2-hydroxypropionate is 95%.

4-Acetoxy-2α-benzoyloxy-5β,20-epoxy-1-hydroxy-9-oxo-7β,10β-bis(2,2,2-trichloroethoxy)-carbonyloxy-11-taxen-13α-yl (2R,3S)-3-t-butoxycarbonylamino-3-phenyl-2-hydroxypropionate is converted to 4-acetoxy-2α-benzoyloxy-5β,20-epoxy-9-oxo-1,7β,10β-trihydroxy-11-taxen-13α-yl (2R,3S)-3-t-butoxycarbonylamino-3-phenyl-2-hydroxypropionate (or Taxotere) under the conditions described in Patent EP 0,253,738.

EXAMPLE 3

A solution of 2.43 g of methyl (2R,3S)-3-t-butoxycarbonylamino-2-hydroxy-3-phenylpropionate and 0.059 g of pyridinium p-toluenesulphonate in 60 cm$^3$ of toluene is dehydrated by distilling off 5 cm$^3$ of solvent. A solution of 1.7 g of 3,4-dimethoxybenzaldehyde dimethyl acetal in 14 cm$^3$ of toluene is added in the course of 15 minutes to the reaction mixture heated to boiling. During the addition, 15 cm$^3$ of toluene are distilled off, and then a further 25 cm$^3$ are distilled off. After cooling to a temperature in the region of 20° C., 40 cm$^3$ of water are added with stirring. After settling has taken place, the organic phase is separated and dried over magnesium sulphate. After filtration and concentration to dryness, the residue is taken up with 8 cm$^3$ of diisopropyl ether. The product which crystallizes is separated by filtration, rinsed with diisopropyl ether and then dried under reduced pressure. 1.7 g of (2R,4S,5R)-3-t-butoxycarbonylamino-2-(3,4-dimethoxyphenyl)-4-phenyl-5-methoxycarbonyl-1,3-oxazolidine, the characteristics of which are as follows, are thereby obtained in a 50% yield:

infrared spectrum (disks, mixed with KBr): characteristic absorption bands at 3085, 3065, 3030, 2975, 2935, 2840, 1740, 1700, 1600, 1520, 1495, 1455, 1425, 1265, 1175, 1025, 800, 755 and 700 cm$^{-1}$ proton nuclear magnetic resonance spectrum (300 MHz; DMSO-d$_6$; chemical shifts a in ppm; coupling constants J in Hz): 1.00 (s, 9H); 3.58 (s, 3H); 3.80 (s, 3H); 3.83 (s, 3H); 4.68 (d, J=4, 1H); 5.31 (unres. comp., 1H); 6.34 (unres. comp., 1H); 6.95 to 7.10 (rot., 3H); 7.35 to 7.50 (mr., 5H).

0.24 g of 86% potassium hydroxide is added to a solution of 1.63 g of the ester thereby obtained in 25 cm$^3$ of methanol and 7 cm$^3$ of distilled water. The mixture is stirred for 40 minutes at a temperature in the region of 20° C. After removal of the methanol by distillation under reduced pressure and acidification of the medium to pH 3–4 by adding 1N hydrochloric acid, the precipitate obtained is separated by filtration. The filter cake is washed with water and then dried. 1.45 g of (2R,4S,5R)-3-t-butoxycarbonyl-2-(3,4-dimethoxyphenyl)-4-phenyl-1,3-oxazolidine-5-carboxylic acid, the purity of which is 95% and the characteristics of which are as follows, are thereby obtained in a 92% yield:

infrared spectrum (disks, mixed with KBr): characteristic absorption bands at 3225, 3030, 3005, 2975, 2930, 2840, 1740, 1710, 1610, 1600, 1515, 1465, 1455, 1260, 1175, 1020, 760 and 700 cm$^{-1}$ proton nuclear magnetic resonance spectrum (250 MHz; DMSO-d$_6$; chemical shifts δ in ppm; coupling constants J in Hz): 1.00 (s, 9H); 3.78 (s, 3H); 3.81 (s, 3H); 4.55 (d, J=4, 1H); 5.23 (unres. comp. 1H); 6.29 (unres. comp., 1H); 6.90 to 7.10 (mt, 3H); 7.30 to 7.50 (mt, 5H).

EXAMPLE 4

0.076 g of dicyclohexylcarbodiimide and 0.0075 g of 4-(dimethylamino)pyridine are added all at once at 0° C. to a stirred suspension of 0.155 g of (2R,4S,5R)-3-t-butoxycarbonyl-2-(3,4-dimethoxyphenyl)-4-phenyl-1,3-oxazolidine-5-carboxylic acid and 0.24 g of 4-acetoxy-2α-benzoyloxy-5β,20-epoxy-1,13α-dihydroxy-9-oxo-7β,10β-bis(2,2,2-trichloroethoxy)carbonyloxy-11-taxene in 2.5 cm$^3$ of anhydrous toluene. The mixture is stirred for 1 hour at 0° C. The dicyclohexylurea formed is separated by filtration. The cake is washed with toluene. The combined toluene phases are washed successively with saturated aqueous sodium bicarbonate solution and then with water. After drying and concentration to dryness under reduced pressure, 0.435 g of 4-acetoxy-2α-benzoyloxy-5β,20-epoxy-1-hydroxy-9-oxo-7β,10β-bis(2,2,2-trichloroethoxy)-carbonyloxy-11-taxen-13α-yl (2R,4S,5R)-3-t-butoxycarbonyl-2-(3,4-dimethoxyphenyl)-4-phenyl-1,3-oxazolidine-5-carboxylate, the characteristics of which are as follows, is obtained in a quantitative yield:

infrared spectrum (CCl$_4$): characteristic absorption bands at 3580, 3550–3375, 3090, 3070, 3030, 1765, 1740, 1730, 1715, 1605, 1520, 1500, 1465, 1455, 1265, 1250, 1180, 1035, 985, 710 and 695 cm$^{-1}$ proton nuclear magnetic resonance spectrum (400 MHz; CDCl$_3$; temperature: 323° K.; chemical shifts δ in ppm; coupling constants J in Hz): 1.10 (s, 9H); 1.17 (s, 3H); 1.25 (s, 3H); 1.66 (s, 3H); 1.70 (s, 1H); 1.82 (s, 3H); 1.90 (s, 3H); 2.02 (mt, 1H); 2.13 (dd, J=15 and 9, 1H); 2.24 (dd, J=15 and 9, 1H); 2.60 (mt, 1H); 3.83 (d, J=7, 1H); 3.89 (s, 3H); 3.93 (s, 3H); 4.12 (d, J=8, 1H); 4.26 (d, J=8, 1H); 4.60 (d, J=4.5, 1H); 4.60 (d, J=12, 1H); 4.78 (limiting ab, 2H); 4.89 (broad d, J=10, 1H); 4.90 (d, J=12, 1H); 5.46 (broad d, J=4.5, 1H); 5.50 (dd, J=11 and 7, 1H); 5.66 (d, J=7, 1H); 6.13 (t, J=9, 1H); 6.15 (s, 1H); 6.39 (s, 1H); 6.90 (d, J=7.5, 1H); 7.03 (d, J=1, 1H); 7.07 (dd, J=7.5 and 1, 1H); 7.35 to 7.50 (mt, 5H); 7.48 (t, J=7.5, 2H); 7.62 (t, J=7.5, 1H); 8.03 (d, J=7.5, 2H).

2 μl of methanesulphonic acid are added to a solution of 0.223 g of the ester obtained above in 2.5 cm$^3$ of methanol. The mixture is stirred for 2 hours 30 minutes at a temperature in the region of 20° C. Assay by high performance liquid chromatography shows that the yield of 4-acetoxy-2α-benzoyloxy-5β,20-epoxy-1-hydroxy-9-oxo-7β,10β-bis (2,2,2-trichloroethoxy)carbonyloxy-11-taxen-13α-yl (2R,3S)-3-t-butoxy-carbonylamino-3-phenyl-2-hydroxypropionate is 88%.

EXAMPLE 5

A solution of 0.497 g of methyl (2R,3S)-3-t-butoxycarbonylamino-2-hydroxy-3-phenylpropionate, 0.012 g of pyridinum b-toluenesulphonate and 0.295 g of 2,4-dimethoxybenzaldehyde in 20 cm³ of anhydrous toluene is heated to reflux for 24 hours. The water formed during the reaction is removed by means of a Dean and Stark apparatus. After cooling to a temperature in the region of 20° C., the solution is washed with 37% (w/w) aqueous sodium hydrogen sulphite solution and then with saturated aqueous sodium bicarbonate solution. After concentration of the organic phase under reduced pressure, 0.700 g of (4S,5R)-3-t-butoxycarbonyl-2-(2,4-dimethoxyphenyl)-4-phenyl-5-methoxycarbonyl-1,3-oxazolidine is obtained in an 80% yield in the form of a virtually equimolecular mixture of the diastereo-isomeric forms A and B, the characteristics of which are as follows:

infrared spectrum (CCl₄): characteristic absorption bands at 3095, 3070, 3035, 2980, 2955, 2935, 2840, 1760, 1745, 1710, 1615, 1590, 1510, 1465, 1455, 1435, 1210, 1160, 1040, 835 and 700 cm⁻¹ proton nuclear magnetic resonance spectrum (250 MHz; DMSO-d₆; chemical shifts δ in ppm; coupling constants J in Hz): 1.00 (s, —C(C$\underline{H}_3$)₃ of B) ; 1.22 (s, —C(C$\underline{H}_3$)₃ of A); 3.55 (unres. comp. —COOC$\underline{H}_3$ or —OC$\underline{H}_3$ of B); 3.87 to 3.85 (mt, —COOC$\underline{H}_3$ or —OC$\underline{H}_3$ of A and B); 4.64 (d, J=4.5, —$\underline{H}$5 of B); 5.01 (d, J=2.5, —$\underline{H}$5 of A); 5.21 (d, J=2.5, —$\underline{H}$4 of A); 5.26 (d, J=4.5, —$\underline{H}$4 of B); 6.46 [dd, J=7.5 and 1.5, —C₆H₅ at position 2 (—$\underline{H}$5) of A]; 6.52 (s, —$\underline{H}$2 of A); 6.50–6.65 [mt, —$\underline{H}$2 and —C₆H₅ at position 2 (—$\underline{H}$5 and —$\underline{H}$3) of B+—C₆H₅ at position 2 (—$\underline{H}$3) of A]; 7.00 [d, J=7.5, —C₆H₅ at position 2 (—$\underline{H}$6) of B]; 7.30 to 7.55 (mt, 5H, —C₆H₅ at position 4 (—$\underline{H}$2 to —$\underline{H}$6) of A and B].

0.073 g of lithium hydroxide monohydrate is added to a solution of 0.700 g of the ester obtained above in a mixture of 9 cm³ of methanol and 3 cm³ of distilled water. The resulting mixture is stirred for 3 hours 30 minutes at a temperature in the region of 20° C. The methanol is removed by distillation under reduced pressure. The aqueous phase is washed with toluene and is then acidified until the pH equals 3–4 by adding 1N aqueous hydrochloric acid solution. The precipitate obtained is separated by filtration, and the filter cake is washed copiously with water to neutrality and then dried under reduced pressure. 0.450 g of (4S,5R)-3-t-butoxycarbonyl-2-(2,4-dimethylphenyl)-4-phenyl-1,3-oxazolidine-5-carboxylic acid is thereby obtained in a 74% yield in the form of a virtually equimolecular mixture of the diastereoisomeric forms A and B, the characteristics of which are as follows:

infrared spectrum (in disk with KBr): characteristic absorption bands at 3300–2700, 2700–2250, 3070, 3030, 3005, 2975, 2940, 2840, 1710, 1615, 1590, 1510, 1460, 1210, 1160, 1035, 835 and 700 cm⁻¹ proton nuclear magnetic resonance spectrum (200 MHz; DMSO-d₆; temperature: 393° K.; chemical shifts δ in ppm; coupling constants J in Hz; mixture of the 2 diastereoisomers in the proportion 55:45): 1.00 (s, —C(C$\underline{H}_3$)₃ of B); 1.25 (s, —C(CH₃)₃ of A); 3.75 to 3.85 (mt, 6H, —OC$\underline{H}_3$ of A and B); 4.43 (d, J=5, —$\underline{H}$5 of B); 4.77 (d, J=2, —$\underline{H}$5 of A); 5.21 (d, J=2, —$\underline{H}$4 of A); 5.21 (d, J=2, —$\underline{H}$4 of B); 6.42 [dd, J=7.5 and 1.5, —C₆H₅ at position 2 (—$\underline{H}$5) of A]; 6.49 (s, —$\underline{H}$2 of A); 6.45–6.60 [mt, $\underline{H}$2 and —C₆H₅ at position 2 (—$\underline{H}$5 and —$\underline{H}$3) of B+—C₆H₅ at position 2 (—$\underline{H}$3) of A]; 7.02 [d, J=7.5, —C₆H₅ at position 2 (—$\underline{H}$6) of A]; 7.15 [d, J=7.5, —C₆H₅ at position 2 (—$\underline{H}$6) of B]; 7.25 to 7.50 [rot, 5H, —C₆H₅ at position 4 (—$\underline{H}$2 to —$\underline{H}$6) of A and B].

EXAMPLE 6

0.656 g of dicyclohexylcarbodiimide and 0.0287 g of 4-(dimethylamino)pyridine are added all at once at 0° C. to a stirred suspension of 1.671 g of (4S,5R)-3-t-butoxycarbonyl-2-(2,4-dimethoxyphenyl)-4-phenyl-1,3-oxazolidine-5-carboxylic acid and 1.003 g of 4-acetoxy-2α-benzoyloxy-5β,20-epoxy-1,13α-dihydroxy-9-oxo-7β,10β-bis(2,2,2-trichloroethoxy) carbonyloxy-11-taxene in 8 cm³ of anhydrous toluene. The mixture is stirred for 10 minutes at 0° C. and then for 5 hours at a temperature in the region of 20° C. The dicyclohexylurea formed is separated by filtration and washed with toluene. The combined toluene phases are washed with saturated aqueous sodium bicarbonate solution and then with water. After drying, filtration and concentration to dryness under reduced pressure, 1.623 g of crude 4-acetoxy-2α-benzoyloxy-5β,20-epoxy-1-hydroxy-9-oxo-7β,10β-bis(2,2,2-trichloroethoxy)carbonyloxy-11-taxen-13α-yl (4S,5R)-3-t-butoxycarbonyl-2-(2,4-dimethoxyphenyl)-4-1,3-oxazolidine-5-carboxylate are obtained in the form of a diastereoisomeric mixture, the constituents of which are separated by liquid chromatography on silica gel, eluting with an ethyl acetate/cyclohexane mixture (75:25 by volume).

One of the two diastereoisomers possesses the following characteristics:

proton nuclear magnetic resonance spectrum (400 MHz; CDCl₃; chemical shifts a in ppm; coupling constants J in Hz): 1.20 (s, 3H); 1.25 (s, 9H); 1.30 (s, 3H); 1.76 (s, 1H); 1.85 (s, 3H); 2.00 (s, 3H); 2.05 (mt, 1H); 2.17 (s, 3H); 2.26 (dd, J=15 and 9, 1H); 2.34 (dd, J =15 and 9, 1H); 2.60 (mt, 1H); 3.82 (s, 3H); 3.92 (s, 3H); 3.95 (d, J=7, 1H); 4.14 (d, J=8, 1H); 4.30 (d, J=8, 1H); 4.62 (d, J=12, 1H); 4.80 (limiting ab, 2H); 4.90 (mt, 1H); 4.92 (mt, 1H); 4.92 (d, J=12, 1H); 5.36 (d, J=2, 1H); 5.63 (dd, J=11 and 7, 1H); 5.70 (d, J=7, 1H); 6.28 (s, 1H); 6.34 (t, J=9, 1H); 6.43 (dd, J=7.5 and 1.5, 1H); 6.51 (d, J=1.5, 1H); 6.69 (s, 1H); 7.16 (d, J=7.5, 1H); 7.35 to 7.50 (mt, 3H); 7.48 (t, J=7.5, 2H); 7.67 (d, J=7.5, 2H); 7.63 (t, J=7.5, 1H); 8.04 (d, J=7.5, 2H).

The other diastereoisomer possesses the following characteristics:

infrared spectrum (CCl₄): characteristic absorption bands at 3580, 3550–3300, 3070, 3030, 1760, 1740, 1710, 1610, 1590, 1510, 1455, 1435, 1260, 1250, 1210, 1180, 1035, 985, 710 and 700 cm⁻¹ proton nuclear magnetic resonance spectrum (400 MHz; CDCl₃; chemical shifts δ in ppm; coupling constants J in Hz): 1.10 [s, 9H: —C(C$\underline{H}_3$)₃]; 11.16 (s, 3H: —C$\underline{H}_3$ 16 or 17); 1.24 (s, 3H: —C$\underline{H}_3$ 16 or 17); 1.53 (s, 3H: —C$\underline{H}_3$ 19); 1.66 (s, 1H: —O$\underline{H}$ 1); 1.82 (s, 3H: —C$\underline{H}_3$ 18); 2.00 (s, 3H: —COC$\underline{H}_3$); 2.00 (mt, 1H: —(CH)—$\underline{H}$6); 2.12 (dd, J=15 and 9, 1H: —(CH)—$\underline{H}$14); 2.24 (dd, J=15 and 9, 1H: —(CH)—$\underline{H}$14); 2.60 (mt, 1H: —(CH)—$\underline{H}$6); 3.82 (d, J=7, 1H: —$\underline{H}$3); 3.82 (s, 3H: —OC$\underline{H}_3$); 3.90 (s, 3H: —OC$\underline{H}_3$); 4.12 (d, J=8, 1H: —(CH)—$\underline{H}$20); 4.26 (d, J=8, 1H: —(CH)—$\underline{H}$20); 4.55 (d, J=4, 1H: $\underline{H}$5'); 4.62 (d, J=12, 1H: —O(CH)—$\underline{H}$ of CCl₃CH₂OCOO at position 7); 4.78 (ab, J=11, 2H: O—C$\underline{H}_2$ of Cl₃CH₂OCOO at position −10); 4.89 (broad d, J=10, 1H: —$\underline{H}$5); 4.89 (d; J=12, 1H: —O(CH)—$\underline{H}$ of Cl₃CCH₂OCOO at position −7); 5.46 (broad d, J=4, 1H: $\underline{H}$4'); 5.50 (dd, J=11 and 7, 1H: —$\underline{H}$7); 5.65 (d, J=7, 1H: —$\underline{H}$2); 6.05 (t, J=9, 1H: —$\underline{H}$13); 6.16 (s, 1H: —$\underline{H}$10); 6.50 [mt, 2H: —C₆H₅ at position 2' (—$\underline{H}$3 and $\underline{H}$5) ]; 6.72 (unres. comp., 1H: $\underline{H}$2'); 7.22 [d, J=7.5, 1H: —C₆H₅ at position 2' (—$\underline{H}$6)]; 7.30 to 7.50 [mt, 5H: —C₆H₅ at position 4' (—$\underline{H}$2 to —$\underline{H}$6)]; 7.48 [t, J=7.5, 2H: —OCOC₆H₅ (—$\underline{H}$3 and —H5)]; 7.63 [t, J=7.5, 1H: —OCOC₆H₅ (—H4)]; 8.03 [d, J=7.5, 2H: —OCOC₆H₅ (—H2 and —H6)].

80 µl of methanesulphonic acid are added to a solution of 1.623 g of the crude ester obtained above in 20 cm³ of methanol. The mixture is stirred for 4 hours at a temperature in the region of 20° C. Assay by high performance liquid chromatography shows that the yield of 4-acetoxy-2α-benzoyloxy-5β,20-epoxy-9-oxo-7β,10β-bis(2,2,2-trichloroethoxy)carbonyloxy-11-taxen-13α-yl (2R,3S)-3-t-butoxycarbonylamino-3-phenyl-2-hydroxypropionate is 88%.

EXAMPLE 7

A solution of 10.0 g of methyl (2R,3S)-3-t-butoxycarbonylamino-2-hydroxy-3-phenylpropionate, 1.0 g of pyridinium p-toluenesulphonate and 5.7 cm³ of benzaldehyde dimethyl acetal in 250 cm³ of anhydrous toluene is heated to reflux. 200 cm³ of solvent are distilled off in the course of 2 hours. The solution is cooled to a temperature in the region of 20° C. and washed with 50 cm³ of water. After settling has taken place, and separation, drying and concentration to dryness of the organic phase, the residue obtained is taken up in 14 cm³ of diisopropyl ether. The slurry obtained is filtered, rinsed and drained. 8.4 g of (2R,4S,5R)-S-t-butoxycarbonylamino-2,4-diphenyl-5-methoxycarbonyl-1,3-oxazolidine are thereby obtained in a 65% yield in the form of a single diastereoisomer, the characteristics of which are as follows:

infrared spectrum (disk, mixed with KBr): characteristic absorption bands at 3250, 3095, 3070, 3030, 2975, 1710, 1500, 1460, 1165, 760 and 700 cm⁻¹ proton nuclear magnetic resonance spectrum (300 MHz; DMSO-d₆; chemical shifts δ in ppm; coupling constants J in Hz): 0.95 (s, 9H); 4.26 (unres. comp., 1H); 5.10 (unres. comp. 1H); 6.20 (s, 1H); 7.25–7.55 (mr, 5H).

1.26 g of 86% potassium hydroxide are added to a solution of 7.07 g of the ester obtained above in 88 cm³ of methanol and 22 cm³ of water. The mixture is stirred overnight at a temperature in the region of 25° C. The methanol is removed by distillation under reduced pressure. The mixture is acidified by adding 1N hydrochloric acid until the pH equals 2. The precipitate obtained is separated by filtration, washed copiously with water to neutrality and then dried under reduced pressure. 7.0 g of (2R,4S,5R)-3-t-butoxycarbonyl-2,4-diphenyl-1,3-oxazolidine-5-carboxylic acid are thereby obtained in a quantitative yield in the form of a single diastereoisomer, the characteristics of which are as follows:

infrared spectrum (disk, mixed with KBr): main characteristic absorption bands at 3080, 3050, 3030, 3005, 2975, 1760, 1695, 1600, 1585, 1490, 1460, 1435, 1175, 760 and 700 cm⁻¹ proton nuclear magnetic resonance spectrum (200 MHz; DMSO-d₆; chemical shifts a in ppm; coupling constants J in Hz): 0.98 (s, 9H); 3.38 (s, 3H); 4.71 (d, J=4, 1H); 5.30 (broad d, J=4, 1H); 6.38 (s, 1H); 7.25 to 7.55 (mt, 5H).

EXAMPLE 8

0.70 g of dicyclohexylcarbodiimide and 0.030 g of 4-(dimethylamino)pyridine are added to a stirred suspension of 1.25 g of (2R,4S,5R)-3-t-butoxycarbonyl-2,4-diphenyl-1,3-oxazolidine-5-carboxylic acid and 1.08 g of 4-acetoxy-2α-benzoyloxy-5β,20-epoxy-1,13α-dihydroxy-9-oxo-7β,10β-bis(2,2,2-trichloroethoxy)-carbonyloxy-11-taxene in 12 cm³ of anhydrous toluene. The mixture is stirred for 24 hours at a temperature in the region of 20° C. The dicyclohexylurea formed is separated by filtration and washed with toluene. The combined organic phases are washed with saturated aqueous sodium bicarbonate solution. After drying and concentration to dryness under reduced pressure, 2.27 g of a crude product are obtained, which product is purified by liquid chromatography on silica gel, eluting with a hexane/ethyl acetate mixture (1:1 by volume). 1.05 g of 4-acetoxy-2α-benzoyloxy-5β,20-epoxy-1-hydroxy-9-oxo-7β,10β-bis (2,2,2-trichloroethoxy)-carbonyloxy-11-taxen-13α-yl (2R, 4S,5R)-3-t-butoxycarbonyl-2,4-diphenyl-1,3-oxazolidine-5-carboxylate are thereby obtained in a 75% yield in the form of a single diastereoisomer, the characteristics of which are as follows:

infrared spectrum (in disk with KBr): main characteristic absorption bands at 3250, 3095, 3070, 3030, 2975, 1710, 1500, 1460, 1165, 760 and 700 cm⁻¹ proton nuclear magnetic resonance spectrum (400 MHz; CDCl₃; chemical shifts δ in ppm; coupling constants J in Hz): 1.05 (s, 9H); 1.15 (s, 3H); 1.25 (s, 3H); 1.63 (s, 3H); 1.73 (s, 1H); 1.80 (s, 3H); 1.87 (unres. comp. 3H); 2.01 (mt, 1H); 2.08 (dd, J=15 and 9, 1H); 2.23 (dd, J=15 and 9, 1H); 2.58 (mt, 1H); 3.81 (d, J=7, 1H); 4.10 (d, J=8, 1H); 4.26 (d, J=8, 1H); 4.60 (d, J=12, 1H); 4.61 (d, J=4, 1H); 4.78 (ab, J=11, 2H); 4.87 (broad d, J=10, 1H); 4.90 (d, J=12, 1H); 5.46 (mr, 1H); 5.50 (dd, J=11 and 7, 1H); 5.63 (d, J =7, 1H); 6.13 (mt, 1H); 6.13 (s, 1H); 6.43 (unres. comp., 1H); 7.35 to 7.50 (mr, 10H); 7.48 (t, J=7.5, 2H); 7.62 (t, J=7.5, 1H); 8.03 (d, J=7.5, 2H).

2.6 µl of methanesulphonic acid are added to a solution of 41 mg of the ester obtained above in 0.4 cm³ of methanol. The mixture is stirred for 48 hours at a temperature in the region of 20° C. Assay by high performance liquid chromatography shows that 4-acetoxy-2α-benzoyloxy-5β,20-epoxy-1-hydroxy-9-oxo-7β, 10β-bis(2,2,2-trichloroethoxy) carbonyloxy-11-taxen-13α-yl (2R,3S)-3-t-butoxycarbonylamino-3-phenyl-2-hydroxy-propionate is obtained in a 50% yield.

EXAMPLE 9

A solution of 10.0 g of methyl (2R,3S)-3-t-butoxycarbonylamino-2-hydroxy-3-phenylpropionate, 0.334 g of pyridinium p-toluenesulphonate and 3.75 cm³ of trimethyl orthoformate in 70 cm³ of toluene is heated to reflux. 4 cm³ of solvent are distilled off. After cooling to a temperature in the region of 20° C. and filtration, the filtrate is concentrated to dryness under reduced pressure. The residue is taken up with 50 cm³ of hexane. The slurry obtained is filtered, rinsed and drained. 4.6 g of (4S,5R)-3-t-butoxycarbonyl-2-methoxy-4-phenyl-5-methoxycarbonyl-1,3-oxazolidine are thereby obtained in a 40% yield in the form of a mixture of diastereoisomers, the characteristics of which are as follows:

infrared spectrum (CH₂Cl₂): characteristic absorption bands at 2980, 2955, 2935, 2840, 1760, 1745, 1710, 1495, 1460, 1440, 1175, 1080 and 1065 cm⁻¹ proton nuclear magnetic resonance spectrum (300 MHz; DMSO-d₆; temperature: 393° K.; chemical shifts δ in ppm; coupling constants J in Hz) on the 65:35 mixture of diastereoisomers: 1.22 (s, 3H); 1.32 (s, 3H); 3.34 (s, 3H); 3.43 (s, 3H); 3.75 (s, 3H); 4.55 (d, J=3, 1H); 4.68 (d, J=8, 1H); 4.98 (d, J=8, 1H); 5.17 (d, J=3, 1H); 6.10 (s, 1H); 6.13 (s, 1H); 7.20 to 7.50 (mt, 5H).

16.1 g of lithium hydroxide monohydrate are added to a solution of 11.27 g of the product obtained above in 85 cm³ of methanol and 28 cm³ of water. The mixture is stirred for 30 minutes at a temperature in the region of 20° C. The methanol is removed by distillation under reduced pressure, and 145 cm³ of water and 245 cm³ of ethyl acetate are then added. The two-phase mixture is cooled to 0° C. with stirring and then acidified with 1N hydrochloric acid until the pH equals 5. The aqueous phase is separated after settling has taken place and extracted with twice 75 cm³ of ethyl acetate. The organic phases are combined and dried over sodium sulphate. After filtration and concentration under reduced pressure at 25° C. to a volume of 50 cm³, 9.80 g of 4-acetoxy-2α-benzoyloxy-5β,20-epoxy-1,13α-dihydroxy-9-oxo-7β,10β-bis(2,2,2-trichloroethoxy)-carbonyloxy-11-taxene, 4.29 g of dicyclohexyl-carbodiimide and 0.25 g of 4-(dimethylamino)pyridine are added to this residual solution at 0° C. The mixture is stirred for 15 minutes at 0° C. for 3 hours at a temperature in the region of 20° C. The dicyclohexylurea formed is separated by filtration and washed with ethyl acetate. The combined organic phases are washed with saturated aqueous sodium bicarbonate solution. After drying and concentration to dryness under reduced pressure, 14.75 g of 4-acetoxy-2α-benzoyloxy-5β,20-epoxy-1-hydroxy-9-oxo-7β,10β-bis(2,2,2-trichloroethoxy) carbonyloxy-11-taxen-13α-yl (4S,5R)-3-t-butoxycarbonyl-2-methoxy-4-phenyl-1,3-oxazolidine-5-carboxylate are obtained in the form of a diastereoisomeric mixture, the characteristics of which are as follows:

infrared spectrum ($CH_2Cl_2$): characteristic absorption bands at 1760, 1725–1710, 1600, 1450, 1245, 1175, 1060, 985 and 815 $cm^{-1}$ proton nuclear magnetic resonance spectrum (400 MHz; $CDCl_3$; temperature: 323° K.; chemical displacements δ in ppm; coupling constants J in Hz): 1.23 (s, 3H); 1.32 (s, 3H); 1.35 (unres. comp., 9H); 1.88 (s, 3H); 1.91 (s, 3H); 2.08 (s, 3H); 2.08 (mt, 1H); 2.26 (split ab, J=15 and 9, 1H); 2.65 (mt, H); 3.65 (s, 3H); 3.92 (d, J=7, 1H); 4.18 (d, J=8, 1H); 4.31 (d, J=8, 1H); 4.64 (d, J=12, 1H); 4.80 (d, J=7, 1H); 4.83 (limiting ab, 2H); 4.95 (broad d, J=10, 1H); 4.95 (d, J=12, 1H); 5.04 (broad d, J=7, 1H); 5.58 (dd, J=11 and 7, 1H); 5.72 (d, J=7, 1H); 6.25 (s, 1H); 6.31 (s, 1H); 6.34 (t, J=9, 1H); 7.30 to 7.55 (mt, 5H); 7.54 (t, J=7.5, 2H); 7.68 (t, J=7.5, 1H); 8.08 (d, J=7.5, 2H).

47 μl of 37% (w/w) hydrochloric acid are added to a stirred solution of 0.617 g of ester obtained above in 7.6 cm³ of ethyl acetate. The mixture is stirred for 20 hours at a temperature in the region of 20° C. Analysis by high performance liquid chromatography shows that 4-acetoxy-2α-benzoyloxy-5β,20-epoxy-1-hydroxy-9-oxo-7β,10β-bis (2,2,2-trichloroethoxy)carbonyloxy-11-taxen-13α-yl (2R, 3S)-3-t-butoxycarbonylamino-3-phenyl-2-hydroxypropionate is obtained in a 53% yield.

EXAMPLE 10

A solution of 4.01 g of methyl (2R,3S)-3-benzoylamino-2-hydroxy-3-phenylpropionate and 0.01 g of pyridinium p-toluenesulphonate in 70 cm³ of toluene is dehydrated by distilling off 30 cm³ of solvent. 30 cm³ of toluene are added and 20 cm³ of solvent are distilled off. After cooling, a solution of 2.57 g of p-methoxybenzaldehyde dimethyl acetal in 6 cm³ of toluene is added. 20 cm³ of toluene are added, and the mixture is then heated for 40 minutes to a temperature in the region of 100° C. while distilling off 60 cm³ of solvent. After cooling, the cloudy solution is filtered through cotton wool and then concentrated to dryness. 6.13 g of a yellowish oil are thereby obtained, which oil is stirred for 12 hours with 30 cm³ of cyclohexane. After filtration on sintered glass and washing of the precipitate with twice 10 cm³ of cyclohexane, 5.09 g of (2R,4S, 5R)-3-benzoyl-2-(4-methoxyphenyl)-4-phenyl-5-methoxycarbonyl-1,3-oxazolidine are obtained in a 91% yield.

25 cm³ of an aqueous solution containing 834 mg of 86% potassium hydroxide are added to a solution of 4.80 g of the product obtained above in 120 cm³ of methanol. The mixture is stirred for 1 hour at a temperature in the region of 20° C. The methanol is removed by distillation under reduced pressure, and 25 cm³ of water and 50 cm³ of isopropyl ether are then added. The aqueous phase is separated after settling has taken place and then washed with twice 25 cm³ of isopropyl ether. The aqueous phase is acidified by adding concentrated hydrochloric acid until the pH equals 1, and 50 cm³ of dichloromethane are then added. After settling has taken place, the aqueous phase is separated and washed with 25 cm³ of dichloromethane. The combined organic phases are washed with 25 cm³ of water and then dried over sodium sulphate. After filtration and concentration to dryness, 4.49 g of (2R,4S,5R)-3-benzoyl-2-(4-methoxyphenyl)-4-phenyl-1,3-oxazolidine-5-carboxylic acid are obtained in a 97% yield.

EXAMPLE 11

A solution of 0.1023 g of (2R,4S,5R)-3-benzoyl-2-(4-methoxyphenyl)-4-phenyl-1,3oxazolidine-5-carboxylic acid and 5.2 mg of 4-(dimethylamino)pyridine in 3 cm³ of toluene is added to a solution of 0.137 g of 85% 4,10β-diacetoxy-2α-benzoyloxy-5β,20-epoxy-1,13α-dihydroxy-9-oxo-7β-triethylsilyloxy-11-taxene and 0.0521 g of dicyclohexylcarbodiimide in 1 cm³ of toluene. The mixture is stirred for 2 hours 15 minutes at a temperature in the region of 20° C. The dicyclohexylurea is separated by filtration. 20 cm³ of saturated sodium bicarbonate solution are added to the filtrate. After settling has taken place, the aqueous phase is separated and extracted with 3 times 30 cm³ of dichloromethane. The combined organic phases are dried over sodium sulphate. After filtration and concentration, 0.2108 g of a product is obtained, which product is purified by chromatography on 7 g of silica contained in a column 30 cm in height and 1.5 cm in diameter, eluting with a cyclohexane/ethyl acetate mixture (70:30 by volume). 127.4 mg of 4,10β-diacetoxy-2α-benzoyloxy-5β,20-epoxy-1-hydroxy-9-oxo-7β-triethylsilyloxy-11-taxen-13α-yl (2R,4S, 5R)-3-benzoyl-2-(4-methoxyphenyl)-4-phenyl-1,3-oxazolidine-5-carboxylate, the structure of which is confirmed by the proton nuclear magnetic resonance spectrum and the purity of which is in the region of 95%, are thereby obtained in a 70.54% yield.

400 μl of a 0.9N ethanolic solution of hydrochloric acid are added to a solution of 40 mg of the product obtained above in 2 cm³ of ethanol. The mixture is stirred for 6 hours at a temperature in the region of 20° C. Assay by high performance liquid chromatography shows that the yield of 4,10β-diacetoxy-2α-benzoyloxy-5β,20-epoxy-1,7β-dihydroxy-9-oxo-11-taxen-13α-yl (2R,3S)-3-benzoyl-3-phenylpropionate (or taxol) is 51.4%.

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims. The above references are hereby incorporated by reference.

We claim:

1. A process for preparing a product of formula (IX):

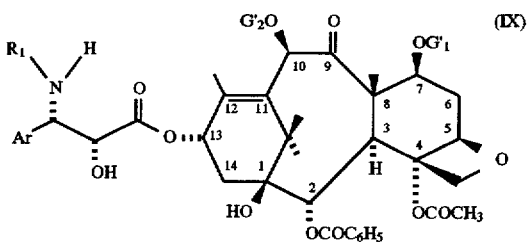

in which

G'₁ represents a hydrogen atom or a group protecting the hydroxyl function,

G'₂ represents a hydrogen atom, an acetyl radical, or a group protecting the hydroxyl function, R₁ represents a benzoyl radical or a radical R₂—O—CO— in which R₂ represents:

an unbranched or branched alkyl radical containing 1 to 8 carbon atoms, an alkenyl radical containing 2 to 8 carbon atoms, an alkynyl radical containing 3 to 8 carbon atoms, a cycloalkyl radical containing 3 to 6 carbon atoms, a cycloalkenyl radical containing 4 to 6 carbon atoms or a bicycloalkyl radical containing 7 to 10 carbon atoms, wherein these radicals defined for R₂ are optionally substituted with at least one substituent selected from halogen atoms, hydroxyl radicals, alkyloxy radicals containing 1 to 4 carbon atoms, dialkylamino radicals in which each alkyl portion contains 1 to 4 carbon atoms, piperidino radicals, morpholino radicals, 1-piperazinyl radicals, said 1-piperazinyl radicals being optionally substituted at position 4 with an alkyl radical containing 1 to 4 carbon atoms or with a phenylalkyl radical in which the alkyl portion contains 1 to 4 carbon atoms, cycloalkyl radicals containing 3 to 6 carbon atoms, cycloalkenyl radicals containing 4 to 6 carbon atoms, phenyl radicals, cyano radicals, carboxyl radicals, and alkyloxycarbonyl radicals in which the alkyl portion contains 1 to 4 carbon atoms, wherein said cycloalkyl, cycloalkenyl and bicycloalkyl radicals can be optionally substituted with at least one alkyl radical containing 1 to 4 carbon atoms, or a phenyl radical optionally substituted with at least one substituent selected from halogen atoms and radicals selected from alkyl radicals containing 1 to 4 carbon atoms and alkyloxy radicals containing 1 to 4 carbon atoms, or a saturated or unsaturated nitrogenous heterocyclic radical containing 5 or 6 ring atoms and being optionally substituted with at least one alkyl radical containing 1 to 4 carbon atoms, and Ar represents a phenyl or α- or β-naphthyl radical optionally substituted with at least one substituent selected from fluorine, chlorine, bromine, and iodine atoms and alkyl, alkenyl, alkynyl, aryl, arylalkyl, alkoxy, alkylthio, aryloxy, arylthio, hydroxyl, hydroxyalkyl, mercapto, formyl, acyl, acylamino, aroylamino, alkoxycarbonylamino, amino, alkylamino, dialkylamino, carboxyl, alkoxycarbonyl, carbamoyl, dialkylcarbamoyl, cyano and trifluoromethyl radicals, wherein the alkyl radicals and alkyl portions of said above radicals independently contain 1 to 4 carbon atoms, and the alkenyl and alkynyl radicals independently contain 3 to 8 carbon atoms and the aryl radicals and aryl portions of said above radicals are independently selected from phenyl and α- and β-naphthyl radicals, said process comprising the steps of:

(A) esterifying a protected 10-deacetylbaccatin III or baccatin III derivative of formula (III):

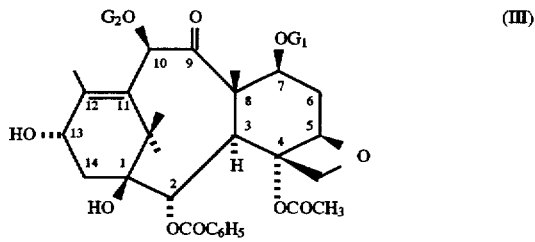

in which G₁ represents a group protecting the hydroxyl function and G₂ represents an acetyl radical or a group protecting the hydroxyl function, by means of an acid or salt of formula (VII):

in which Ar and R₁ are defined as above and R₃ represents a hydrogen atom, an alkoxy radical containing 1 to 4 carbon atoms, or an optionally substituted aryl radical, or by means of a derivative of said acid of formula (VII), to obtain a product of formula (VIII):

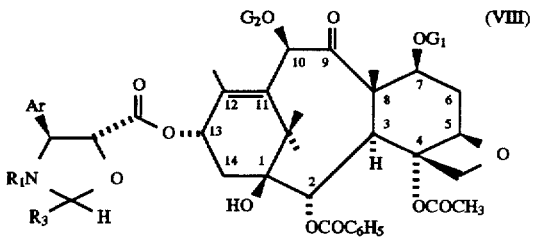

in which Ar, R₁, R₃, G₁ and G₂ are defined as above, (B) deprotecting the side chain of said product of formula (VIII) and (C) optionally deprotecting at least one of the G₁ and G₂-protected hydroxyl functions of said product of formula (VIII), to obtain said product of formula (IX).

2. Process according to claim 1, wherein the esterification is performed by means of an acid of formula VII or one of its derivatives for which, Ar and R₁ are defined as in claim 1, R₃ represents a hydrogen atom or an alkoxy radical containing 1 to 4 carbon atoms or a phenyl radical optionally substituted with electron-donating radical.

3. Process according to claim 2, wherein the electron-donating radicals are selected from alkoxy radicals containing 1 to 4 carbon atoms.

4. Process according to claim 1, wherein the groups protecting baccatin III or 10-deacetylbaccatin III represented by G₁ and G₂ are selected from (2,2,2-trichloroethoxy)carbonyl and 2-(2-trichloromethylpropoxy)carbonyl radicals and trialkylsilyl, dialkylarylsilyl, alkyldiarylsilyl or triarylsilyl radicals in which the alkyl portions contain 1 to 4 carbon atoms and the aryl portions are phenyl radicals.

5. Process according to claim 1, wherein the esterification by means of an acid of formula (VII):

 (VII)

in which Ar and $R_1$ are defined as in claim 1 and $R_3$ is defined as in claim 1, is performed in the presence of a condensing agent and an activating agent, working in an organic solvent at a temperature of from −10° to 90° C.

6. Process according to claim 5, wherein the condensing agent is selected from carbodiimides and reactive carbonates and the activating agent is selected from aminopyridines.

7. Process according to claim 6, wherein the condensing agent is selected from dicyclohexylcarbodiimide and di-2-pyridyl carbonate and the activating agent is selected from 4-(dimethylamino)-pyridine and 4-pyrrolidinopyridine.

8. Process according to claim 5, wherein the solvent is selected from ethers, ketones, esters, nitriles, aliphatic hydrocarbons, halogenated aliphatic hydrocarbons and aromatic hydrocarbons.

9. Process according to claim 8, wherein the solvent is selected from aromatic hydrocarbons.

10. Process according to claim 1 wherein, said derivative of said acid of formula (VII) is an anhydride of formula (X):

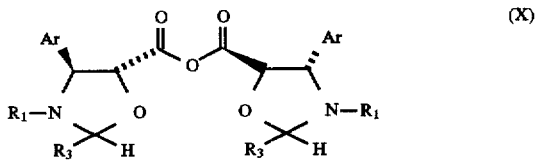 (X)

in which Ar and $R_1$ are defined as in claim 1 and $R_3$ is defined in claim 1, wherein said step of esterification is carried out in the presence of an activating agent in an organic solvent at a temperature ranging from 0° to 90° C.

11. Process according to claim 10, wherein the activating agent is selected from aminopyridines.

12. Process according to claim 11, wherein the activating agent is selected from 4-(dimethylamino)pyridine and 4-pyrrolidinopyridine.

13. Process according to claim 10, wherein the solvent is selected from ethers, ketones, esters, nitriles, aliphatic hydrocarbons, halogenated aliphatic hydrocarbons and aromatic hydrocarbons.

14. Process according to claim 1 wherein, said derivative of said acid of formula (VII) is an activated acid of formula (XI):

 (XI)

in which Ar and $R_1$ are defined as in claim 1 and $R_3$ is defined in claim 1 and X represents a halogen atom or an acyloxy or aryloxy radical, optionally prepared in situ, wherein said step of esterification is carried out in the presence of a base in an organic solvent at a temperature ranging from 10° to 80° C.

15. Process according to claim 14, wherein the base is selected from nitrogenous organic bases.

16. Process according to claim 15, wherein the nitrogenous organic base is selected from aliphatic tertiary amines, pyridine and aminopyridines.

17. Process according to claim 14, wherein the solvent is selected from ethers, ketones, esters, nitriles, aliphatic hydrocarbons, halogenated aliphatic hydrocarbons and aromatic hydrocarbons.

18. Process according to claim 17, wherein the solvent is selected from aromatic hydrocarbons.

19. Process according to claim 1 wherein, said protecting groups $G_1$ and $G_2$ are silyl protective groups and wherein the deprotection of the side chain and, optionally, of the hydroxyl functions protected by said silyl protective groups $G_1$ and $G_2$ is performed in the presence of an inorganic or organic acid or mixtures thereof, working in an organic solvent at a temperature ranging from −10° to 60° C.

20. Process according to claim 19, wherein the inorganic acid is selected from hydrochloric and sulphuric acids and the organic acid is selected from acetic, methanesulphonic, trifluoromethanesulphonic and p-toluenesulphonic acids.

21. Process according to claim 19, wherein the solvent is selected from alcohols, ethers, esters, nitriles, aliphatic hydrocarbons, halogenated aliphatic hydrocarbons and aromatic hydrocarbons.

22. Process according to claim 1, wherein the deprotection of the side chain is performed in the presence of an oxidizing agent in water or in an aqueous-organic medium.

23. Process according to claim 22, wherein the oxidizing agent is ammonium cerium IV nitrate in an aqueous-organic medium.

24. Process according to claim 22, wherein the aqueous-organic medium is a water/acetonitrile mixture.

25. Process according claim 22, wherein the oxidizing agent is 2,3-dichloro-5,6-dicyano-1,4-benzoquinone in water.

26. Process according to claim 1, wherein the deprotection of the side chain is performed by hydrogenolysis.

27. Process according to claim 26, wherein the hydrogenolysis is performed with hydrogen in the presence of a catalyst.

28. Process according to claim 1, wherein replacement by a hydrogen atom of the protective group $G_1$ and optionally, the group $G_2$, wherein $G_2$ represents a 2,2,2-trichloroethoxycarbonyl or 2-(2-trichloromethyl-propoxy) carbonyl radical is performed with zinc, optionally in the presence of acetic acid at a temperature from 20° to 60° C., or by means of an acid dissolved in an aliphatic alcohol containing 1 to 3 carbon atoms or in an aliphatic ester, in the presence of zinc optionally in combination with copper.

29. An acid of formula (VII):

 (VII)

in which Ar and $R_1$ are defined as in claim 1 and $R_3$ is defined in claim 1, optionally in the form of a salt, ester, anhydride, mixed anhydride or halide.

21

30. A product of general formula (VII):

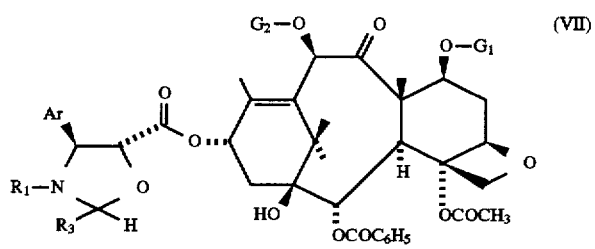

in which Ar and $R_1$ are defined as in claim 1, $R_3$ is defined in claim 1 and $G_1$ and $G_2$ are defined in claim 1.

31. A process according to claim 1, wherein in said formula (III), $G_2$ represents an acetyl radical, and further wherein in said formula (IX), $G'_2$ represents an acetyl radical.

32. A process according to claim 1, wherein said derivative of said acid of formula (VII) is an ester, an anhydride, a mixed anhydride or a halide.

33. A process according to claim 1, wherein in said optional step (C), the $G_1$-protected hydroxyl function of said product of formula (VIII) is deprotected to obtain a taxane derivative of formula (I).

34. A process for preparing a product of formula (VIII):

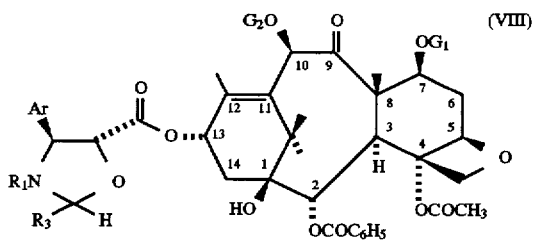

in which $G_1$ represents a group protecting the hydroxyl function $G_2$ represents an acetyl radical or a group protecting the hydroxyl function, Ar represents a phenyl or α- or β-naphthyl radical optionally substituted with at least one substituent selected from fluorine, chlorine, bromine, and iodine atoms and alkyl, alkenyl, alkynyl, aryl, arylalkyl, alkoxy, alkylthio, aryloxy, arylthio, hydroxyl, hydroxyalkyl, mercapto, formyl, acyl, acylamino, aroylamino, alkoxycarbonylamino, amino, alkylamino, dialkylamino, carboxyl, alkoxycarbonyl, carbamoyl, dialkylcarbamoyl, cyano and trifluoromethyl radicals, wherein the alkyl radicals and alkyl portions of said above radicals independently contain 1 to 4 carbon atoms, and the alkenyl and alkynyl radicals independently contain 3 to 8 carbon atoms and the aryl radicals and aryl portions of said above radicals are independently selected from phenyl and α- and β-naphthyl radicals, $R_1$ represents a benzoyl radical or a radical $R_2$—O—CO— in which $R_2$ represents:

an unbranched or branched alkyl radical containing 1 to 8 carbon atoms, an alkenyl radical containing 2 to 8 carbon atoms, an alkynyl radical containing 3 to 8 carbon atoms, a cycloalkyl radical containing 3 to 6 carbon atoms, a cycloalkenyl radical containing 4 to 6 carbon atoms or a bicycloalkyl radical containing 7 to 10 carbon atoms, wherein these radicals defined for $R_2$ are optionally substituted with at least one substituent selected from halogen atoms, hydroxyl radicals, alkyloxy radicals

22 containing 1 to 4 carbon atoms, dialkylamino radicals in which each alkyl portion contains 1 to 4 carbon atoms, piperidino radicals, morpholino radicals, 1-piperazinyl radicals, said 1-piperazinyl radicals being optionally substituted at position 4 with an alkyl radical containing 1 to 4 carbon atoms or with a phenylalkyl radical in which the alkyl portion contains 1 to 4 carbon atoms, cycloalkyl radicals containing 3 to 6 carbon atoms, cycloalkenyl radicals containing 4 to 6 carbon atoms, phenyl radicals, cyano radicals, carboxyl radicals, and alkyloxycarbonyl radicals in which the alkyl portion contains 1 to 4 carbon atoms, wherein said cycloalkyl, cycloalkenyl and bicycloalkyl radicals can be optionally substituted with at least one alkyl radical containing 1 to 4 carbon atoms, or a phenyl radical optionally substituted with at least one substituent selected from halogen atoms and radicals selected from alkyl radicals containing 1 to 4 carbon atoms and alkyloxy radicals containing 1 to 4 carbon atoms, or a saturated or unsaturated nitrogenous heterocyclic radical containing 5 or 6 ring atoms and being optionally substituted with at least one alkyl radical containing 1 to 4 carbon atoms, and $R_3$ represents a hydrogen atom, an alkoxy radical containing 1 to 4 carbon atoms, or an optionally substituted aryl radical, said process comprising the step of:

esterifying a protected 10-deacetylbaccatin III or baccatin III derivative of formula (III):

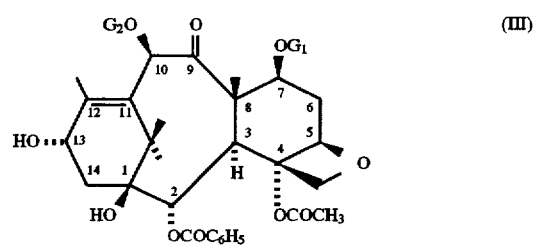

in which $G_1$ and $G_2$ are as defined above by means of an acid or salt of formula (VII):

in which Ar, $R_1$ and $R_3$ are defined as above,
or by means of a derivative of said acid of formula (VII), to obtain said product of formula (VIII).

35. A process for preparing a product of formula (IX):

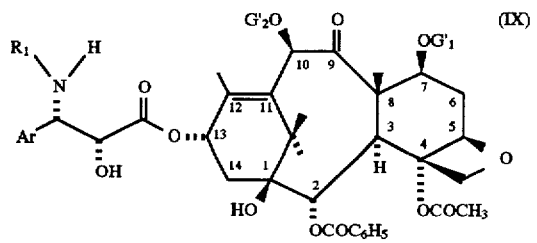

in which $G'_1$ represents a hydrogen atom or a group protecting the hydroxyl function, G'$_2$ represents a hydrogen atom, an acetyl radical, or a group protecting the hydroxyl function, R$_1$ represents a benzoyl radical or a radical R$_2$—O—CO— in which R$_2$ represents:

an unbranched or branched alkyl radical containing 1 to 8 carbon atoms, an alkenyl radical containing 2 to 8 carbon atoms, an alkynyl radical containing 3 to 8 carbon atoms, a cycloalkyl radical containing 3 to 6 carbon atoms, a cycloalkenyl radical containing 4 to 6 carbon atoms or a bicycloalkyl radical containing 7 to 10 carbon atoms, wherein these radicals defined for R$_2$ are optionally substituted with at least one substituent selected from halogen atoms, hydroxyl radicals, alkyloxy radicals containing 1 to 4 carbon atoms, dialkylamino radicals in which each alkyl portion contains 1 to 4 carbon atoms, piperidino radicals, morpholino radicals, 1-piperazinyl radicals, said 1-piperazinyl radicals being optionally substituted at position 4 with an alkyl radical containing 1 to 4 carbon atoms or with a phenylalkyl radical in which the alkyl portion contains 1 to 4 carbon atoms, cycloalkyl radicals containing 3 to 6 carbon atoms, cycloalkenyl radicals containing 4 to 6 carbon atoms, phenyl radicals, cyano radicals, carboxyl radicals, and alkyloxycarbonyl radicals in which the alkyl portion contains 1 to 4 carbon atoms, wherein said cycloalkyl, cycloalkenyl and bicycloalkyl radicals can be optionally substituted with at least one alkyl radical containing 1 to 4 carbon atoms, or a phenyl radical optionally substituted with at least one substituent selected from halogen atoms and radicals selected from alkyl radicals containing 1 to 4 carbon atoms and alkyloxy radicals containing 1 to 4 carbon atoms, or a saturated or unsaturated nitrogenous heterocyclic radical containing 5 or 6 ring atoms and being optionally substituted with at least one alkyl radical containing 1 to 4 carbon atoms, and Ar represents a phenyl or α- or β-naphthyl radical optionally substituted with at least one substituent selected from fluorine, chlorine, bromine, and iodine atoms and alkyl, alkenyl, alkynyl, aryl, arylalkyl, alkoxy, alkylthio, aryloxy, arylthio, hydroxyl, hydroxyalkyl, mercapto, formyl, acyl, acylamino, aroylamino, alkoxycarbonylamino, amino, alkylamino, dialkylamino, carboxyl, alkoxycarbonyl, carbamoyl, dialkylcarbamoyl, cyano and trifluoromethyl radicals, wherein the alkyl radicals and alkyl portions of said above radicals independently contain 1 to 4 carbon atoms, and the alkenyl and alkynyl radicals independently contain 3 to 8 carbon atoms and the aryl radicals and aryl portions of said above radicals are independently selected from phenyl and α- and β-naphthyl radicals, said process comprising the steps of:

(A) deprotecting the side chain of a product of formula (VIII):

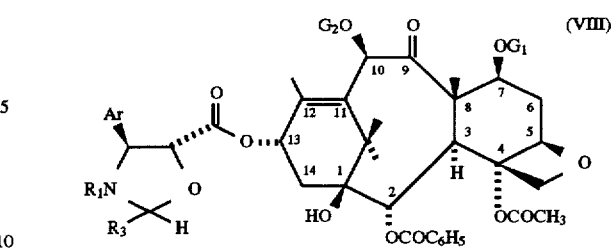

in which

Ar represents a phenyl or α- or β-naphthyl radical optionally substituted with at least one substituent selected from fluorine, chlorine, bromine, and iodine atoms and alkyl, alkenyl, alkynyl, aryl, arylalkyl, alkoxy, alkylthio, aryloxy, arylthio, hydroxyl, hydroxyalkyl, mercapto, formyl, acyl, acylamino, aroylamino, alkoxycarbonylamino, amino, alkylamino, dialkylamino, carboxyl, alkoxycarbonyl, carbamoyl, dialkylcarbamoyl, cyano and trifluoromethyl radicals, wherein the alkyl radicals and alkyl portions of said above radicals independently contain 1 to 4 carbon atoms, and the alkenyl and alkynyl radicals independently contain 3 to 8 carbon atoms and the aryl radicals and aryl portions of said above radicals are independently selected from phenyl and α- and β-naphthyl radicals, R$_1$ represents a benzoyl radical or a radical R$_2$—O—CO— in which R$_2$ represents:

an unbranched or branched alkyl radical containing 1 to 8 carbon atoms, an alkenyl radical containing 2 to 8 carbon atoms, an alkynyl radical containing 3 to 8 carbon atoms, a cycloalkyl radical containing 3 to 6 carbon atoms, a cycloalkenyl radical containing 4 to 6 carbon atoms or a bicycloalkyl radical containing 7 to 10 carbon atoms, wherein these radicals defined for R$_2$ are optionally substituted with at least one substituent selected from halogen atoms, hydroxyl radicals, alkyloxy radicals containing 1 to 4 carbon atoms, dialkylamino radicals in which each alkyl portion contains 1 to 4 carbon atoms, piperidino radicals, morpholino radicals, 1-piperazinyl radicals, said 1-piperazinyl radicals being optionally substituted at position 4 with an alkyl radical containing 1 to 4 carbon atoms or with a phenylalkyl radical in which the alkyl portion contains 1 to 4 carbon atoms, cycloalkyl radicals containing 3 to 6 carbon atoms, cycloalkenyl radicals containing 4 to 6 carbon atoms, phenyl radicals, cyano radicals, carboxyl radicals, and alkyloxycarbonyl radicals in which the alkyl portion contains 1 to 4 carbon atoms, wherein said cycloalkyl, cycloalkenyl and bicycloalkyl radicals can be optionally substituted with at least one alkyl radical containing 1 to 4 carbon atoms, or a phenyl radical optionally substituted with at least one substituent selected from halogen atoms and radicals selected from alkyl radicals containing 1 to 4 carbon atoms and alkyloxy radicals containing 1 to 4 carbon atoms, or a saturated or unsaturated nitrogenous heterocyclic radical containing 5 or 6 ring atoms and being optionally substituted with at least one alkyl radical containing 1 to 4 carbon atoms, R$_3$ represents a hydrogen atom, an alkoxy radical containing 1 to 4 carbon atoms, or an optionally substituted aryl radical, G₁ represents a group protecting the hydroxyl function, and G₂ represents an acetyl radical or a group protecting the hydroxyl function, and (B) optionally deprotecting at least one of the G₁ and G₂-protected hydroxyl functions of said product of formula (VIII), to obtain said product of formula (IX).

36. A process for preparing a taxane derivative of formula (I):

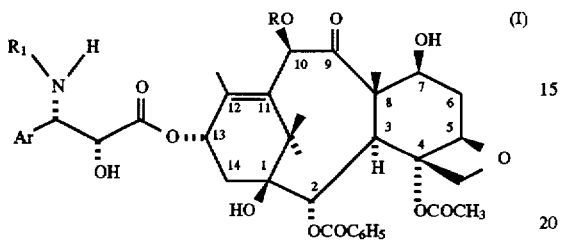

in which

R represents a hydrogen atom, an acetyl radical, or a group protecting the hydroxyl function, and R₁ represents a benzoyl radical or a radical R₂—O—CO— in which R₂ represents:

an unbranched or branched alkyl radical containing 1 to 8 carbon atoms, an alkenyl radical containing 2 to 8 carbon atoms, an alkynyl radical containing 3 to 8 carbon atoms, a cycloalkyl radical containing 3 to 6 carbon atoms, a cycloalkenyl radical containing 4 to 6 carbon atoms or a bicycloalkyl radical containing 7 to 10 carbon atoms, wherein these radicals defined for R₂ are optionally substituted with at least one substituent selected from halogen atoms, hydroxyl radicals, alkyloxy radicals containing 1 to 4 carbon atoms, dialkylamino radicals in which each alkyl portion contains 1 to 4 carbon atoms, piperidino radicals, morpholino radicals, 1-piperazinyl radicals, said 1-piperazinyl radicals being optionally substituted at position 4 with an alkyl radical containing 1 to 4 carbon atoms or with a phenylalkyl radical in which the alkyl portion contains 1 to 4 carbon atoms, cycloalkyl radicals containing 3 to 6 carbon atoms, cycloalkenyl radicals containing 4 to 6 carbon atoms, phenyl radicals, cyano radicals, carboxyl radicals, and alkyloxycarbonyl radicals in which the alkyl portion contains 1 to 4 carbon atoms, wherein said cycloalkyl, cycloalkenyl and bicycloalkyl radicals can be optionally substituted with at least one alkyl radical containing 1 to 4 carbon atoms, or a phenyl radical optionally substituted with at least one substituent selected from halogen atoms and radicals selected from alkyl radicals containing 1 to 4 carbon atoms and alkyloxy radicals containing 1 to 4 carbon atoms, or a saturated or unsaturated nitrogenous heterocyclic radical containing 5 or 6 ring atoms and being optionally substituted with at least one alkyl radical containing 1 to 4 carbon atoms, and Ar represents a phenyl or α- or β-naphthyl radical optionally substituted with at least one substituent selected from fluorine, chlorine, bromine, and iodine atoms and alkyl, alkenyl, alkynyl, aryl, arylalkyl, alkoxy, alkylthio, aryloxy, arylthio, hydroxyl, hydroxyalkyl, mercapto, formyl, acyl, acylamino, aroylamino, alkoxycarbonylamino, amino, alkylamino, dialkylamino, carboxyl, alkoxycarbonyl, carbamoyl, dialkylcarbamoyl, cyano and trifluoromethyl radicals, wherein the alkyl radicals and alkyl portions of said above radicals independently contain 1 to 4 carbon atoms, and the alkenyl and alkynyl radicals independently contain 3 to 8 carbon atoms and the aryl radicals and aryl portions of said above radicals are independently selected from phenyl and α- and β-naphthyl radicals, said process comprising the steps of:

(A) esterifying a protected 10-deacetylbaccatin III or baccatin III derivative of formula (III):

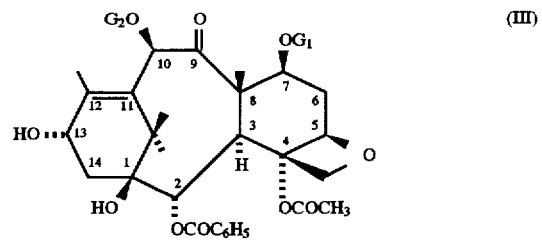

in which G₁ represents a group protecting the hydroxyl function and G₂ represents an acetyl radical or a group protecting the hydroxyl function, by means of an acid or salt of formula (VII):

in which Ar and R₁ are defined as above and R₃ represents a hydrogen atom, an alkoxy radical containing 1 to 4 carbon atoms, or an optionally substituted aryl radical, or by means of a derivative of said acid of formula (VII), to obtain a product of formula (VIII):

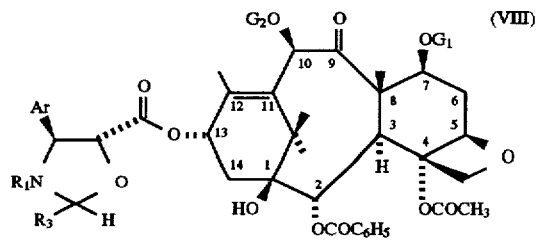

in which Ar, R₁, R₃, G₁ and G₂ are defined as above, (B) deprotecting the side chain of said product of formula (VIII)

(C) deprotecting the G₁-protected hydroxyl function of said product of formula (VIII), and (D) optionally deprotecting the G₂-protected hydroxyl function of said product of formula (VIII), to obtain said taxane derivative of formula (I).

* * * * *

UNITED STATES PATENT AND TRADEMARK OFFICE
CERTIFICATE OF CORRECTION

PATENT NO. : 5,637,723
DATED : June 10, 1997
INVENTOR(S) : Alain COMMERCON et al.

It is certified that error appears in the above-indentified patent and that said Letters Patent is hereby corrected as shown below:

Claim 2, column 18, line 56, after "substituted with", insert --at least one--.

Claim 25, column 20, line 36, after "according", insert --to--.

Claim 30, column 21, line 1, after "product of", delete "general"; and "(VII)" should read --(VIII)--.

Claim 30, column 21, line 3, to the right of the chemical structure, "(VII)" should read --(VIII)--.

Claim 31, column 21, line 15, "(1II)" should read --(III)--.

Signed and Sealed this

Thirtieth Day of September, 1997

Attest:

BRUCE LEHMAN

Attesting Officer

Commissioner of Patents and Trademarks